(12) United States Patent
Park et al.

(10) Patent No.: US 7,192,581 B2
(45) Date of Patent: Mar. 20, 2007

(54) LACTOBACILLUS REUTERI USEFUL AS PROBIOTICS

(75) Inventors: Yong-Ha Park, Seoul (KR); Young-Hyo Chang, Daejon (KR); In-Sun Lee, Suwon (KR); Jung-Hoon Yoon, Daejon (KR); Chul-Joong Kim, Daejon (KR)

(73) Assignee: Probionic Corp., Daejon (KR)

( * ) Notice: Subject to any disclaimer, the term of this patent is extended or adjusted under 35 U.S.C. 154(b) by 198 days.

(21) Appl. No.: 10/657,814

(22) Filed: Sep. 8, 2003

(65) Prior Publication Data

US 2004/0175372 A1 Sep. 9, 2004

(30) Foreign Application Priority Data

Mar. 7, 2001 (KR) ............... 10-2001-1011797
Dec. 31, 2001 (WO) ............ PCT/KR2001/002310

(51) Int. Cl.
*A61K 45/00* (2006.01)
*A61K 35/74* (2006.01)
*C12N 1/20* (2006.01)

(52) U.S. Cl. ............... 424/93.45; 435/252.9
(58) Field of Classification Search ......... 435/252.9, 435/93.45
See application file for complete search history.

(56) References Cited

U.S. PATENT DOCUMENTS 5,540,924 A   7/1996   Ajinomoto
6,849,256 B1 *  2/2005   Farmer ............... 424/93.46

FOREIGN PATENT DOCUMENTS

EP     0955061 A1   11/1999
WO   WO 9746104 A1   12/1997

OTHER PUBLICATIONS

International Search Report PCT/KR01/02310.

* cited by examiner

*Primary Examiner*—Herbert J. Lilling
(74) *Attorney, Agent, or Firm*—Graybeal Jackson Haley LLP

(57) ABSTRACT

The present invention relates to a *Lactobacillus reuteri* variant from animal sources that inhibits rotavirus infection and other pathogenic microorganisms, as well as being tolerant of gastric and bile acids. Also, this invention relates to a prophylactic and therapeutic composition comprising the same for contributing in many probiotic ways to the host's general health and preventing and treating diseases or conditions associated with rotavirus and other enteric pathogens.

9 Claims, No Drawings

LACTOBACILLUS REUTERI USEFUL AS PROBIOTICS

This application claims priority from PCT Patent Application No. PCT/KR01/02310 filed 31 Dec. 2001, which claims priority from Korean patent appliction No. 2001-1111797 filed 7 Mar. 2001. Both patent applications are incorporated herein by reference.

TECHNICAL FIELD

The present invention relates, in general, to a novel probiotic microorganism and, more particularly, to a *Lactobacillus reuteri* variant from animal sources that inhibits rotavirus infection and other pathogenic microorganisms, as well as being tolerant of gastric and bile acids. Also, this invention relates to a prophylactic and therapeutic composition comprising the same for contributing in many probiotic ways to the host's general health and preventing and treating diseases or conditions associated with rotavirus and other enteric pathogens.

BACKGROUND ART

Diarrhea is one of the most common infectious diseases in the world. Although various viral, bacterial, and parasitic agents are suspected of causing acute infectious diarrhea and gastroenteritis, rotaviruses have been identified as the most important viral agent of diarrhea and gastroenteritis, e.g., in children and young animals in both developed and developing countries.

Rotaviruses cause 35–50% of severe diarrheal episodes in infants and young children in both developed and developing countries, and are the most important etiological agents of severe diarrhea in this age group. Rotaviruses are also the most important viral agents causing diahrrea in many animals, including swine units. Diarrhea caused by rotavirus is usually watery to pasty in consistency and may vary considerably in color. Affected pigs are usually depressed, off-feed, and dehydrated. Rotavirus destroys villi in the small intestine, hence, the clinical signs seen in diahrreal outbreaks. Additionally, rotaviruses have been linked with the occurrence of gasteroenteritis and the secondary infections by enteric bacteria in affected animals. That is, rotavirus infections are more difficult to treat when accompanied by secondary bacteria, thereby, enhancing the severity of the outbreak. Treatments for rotavirus are based on supportive treatment that addresses dehydration and starvation that occurs with a rotavirus infection. Treatments with antibiotics are only effective against secondary bacterial infections, and disadvantageous in that antibiotics may remain in the meat. Vaccination may be effective for the prevention of rotaviral infection, but may generate side effects.

Bacteria residing in the intestine may also cause diseases in the colonized host such as diarrhea in the intestines. A wide variety of microorganisms exist in the intestines of humans and animals, constituting intestinal microflora. They include bacteria that are not only beneficial to hosts, like lactic acid bacteria, but also some which are potentially or directly harmful to hosts, like *E. coli, Salmonella, Staphylococcus*, etc. Changes in the external environment, such as increased stress, infection of harmful microorganisms, and the like, may upset the normal balance of the intestinal microflora, resulting in the predominance of harmful microorganisms over beneficial ones. A shift in microflora can lead to abnormal health states of the host, such as diarrhea and, at the worst, even to death. When numbers of harmful microbes reach high levels in the intestine, the host is usually treated by the administration of antibiotics. Although they may be effective for the control of harmful microorganisms, antibiotics are not completely discharged from the host, but partially remain in the host's tissues. Additionally, extended administration of antibiotics induces antibiotic resistance in harmful microorganisms, making it finally impossible to effectively treat diseases they cause. Furthermore, recent legislation in response to environmental concerns stemming from food hygiene has been enacted to substantially lower the acceptable levels of antibiotics present in meats, milks and eggs of livestock. Hence, problems may occur upon use of antibiotics, let alone misuse or abuse thereof.

Thus, there is an urgent need to develop methods of treating and preventing infectious diarrhea caused by enteric viruses and microorganisms, and diahrrea associated with antibiotic theraphy.

There has been an increased interest for microbial species which can beneficially affect the microbial balance of the host, e.g. by producing antimicrobial components or by competitive growing.

Probiotics are a class of microorganisms that are defined as live microbial organisms that beneficially affect the animal and human hosts. The beneficial effects include improvement of the microbial balance of the intestinal microflora or by improving the properties of the indigenous microflora. A better understanding of probiotics in man and animals can be found in the following publication(Fuller R: Probiotics in Man and Animals, J Appl. Bacteriol 1989;66: 365–378). Referring to the use of microorganisms in a positive way to benefit health, probiotics are prepared by formulating beneficial microorganisms that inhabit the intestine. Examples of microorganisms available for the preparation of probiotics include aerobes, anaerobes, lactic acid bacteria, and yeasts with lactic acid bacteria being the most popular. Probiotics enjoy the advantage of causing no side effects such as those resulting from the abuse of antibiotics, and inhibiting the abnormal proliferation of harmful microorganisms to maintain normal intestinal flora and to prevent the occurrence of illness. The known benefits of enteral administration of probiotic microorganisms include enhanced host defense to disease, improving colonization resistance of the harmful microflora and numerous other areas of health promotion. Probiotics have been suggested to play an important role in the formation or establishment of a well-balanced, indigenous, intestinal microflora in newborn children or adults receiving high doses of antibiotics.

For the prevention and treatment of diarrhea in livestock or poultry, live bacterial compositions have been developed for use as agents other than antibiotics. In live bacterial compositions, useful live bacteria are directly administered to livestock or poultry, where the bacteria are retained in the intestine of livestock or antagonize enterotoxic bacteria, e.g., *Escherichia coli*, to eliminate the enterotoxic bacteria, during passage of the live bacteria through the intestine. As a result, the enterobacteria microflora is improved so that diarrhea of livestock is prevented and treated. In addition, research results disclose that persistent administration of probiotics to livestock give rise to an increase in feed efficiency and weight gain.

For effective use, probiotics must be resistant to acid, particularly gastric and bile acid, in addition to having inhibitory activity against harmful microorganisms. Because probiotics are usually consumed in specially designed foods that are variously called nutraceuticals or functional foods, they experience acidic environments, first in gastric juice, a strong acid, and then in bile, until arrival at the intestine. In general, bacteria are killed or deactivated by gastric juice and bile acid. Therefore, probiotics must survive gastric juice and bile to reach the intestine, thereby exerting their beneficial functions.

Various kinds of lactic acid bacteria have been already disclosed as probiotics. Lactobacilli have been among the most studied species, and have in certain instances been shown to counteract the proliferation of pathogens. In fact, *Lactobacillus* therapy have increased in recent years with findings that probiotic *Lactobacillus* (a) improves the intersterial microflora, (b) prevents diarrhea, (c) affords protection from colon cancer for human populations, (d) reduces the incidence of experimentally induced large tumors in rats, (e) reduces the fecal concentraction of bacterial enzymes known to catalyze the conversion of procarcinogens to proximal carcinogens in humans, and (f) reduces the serum cholesterol levels in swine. In recent, a lactic acid bacterium, identified as *Lactobacillus reuteri* BSA-131, was reported to be tolerant of gastric and bile acids as well as inhibiting the proliferation of harmful microorganisms in the intestine (Chang, et al., Korean J. Appl. Microbiol. Biotechnol., 27, 23–27; Korean Pat. No. 10-211529-0000).

DISCLOSURE OF THE INVENTION

Leading to the present invention, the intensive and thorough research into a novel strain with more potent probiotic activity, conducted by the present inventors, resulted in the finding that a bacterial strain anaerobically separated from swine excrements has superb inhibitory activity against harmful microorganisms, including rotavirus, with superior tolerance to gastric and bile acids over the conventional *Lactobacillus reuteri* BAS-131 claimed in Korean Pat. No. 10-211529-0000. The novel bacterial strain was identified as a member of *Lactobacillus reuteri*.

So, the invention demonstrates the effectiveness of a novel probiotic lactic acid bacterium in inhibiting the growth of rotavirus and other enteric pathogenic microorganisms, and thereby preventing their infections.

The present invention describes lactic acid bacteria isolated from the gastro-intestinal tract in pigs and selected by means of, among others, the inhibitory activity against pathogenic microorganisms in vitro and tolerance against acid and bile.

Therefore, it is an object of the present invention to provide a novel enteric bacterial strain, which is tolerant of gastric and bile acids and harmless to humans and animals.

It is another object of the present invention to provide probiotics for use in foods, medicines for humans and livestock, and feedstock, which exhibits excellent inhibitory activity against the growth of harmful microorganisms, especially rotavirus, in the intestine.

It is a further object of the present invention to provide a method for inhibiting the growth of rotavirus and other harmful microorganisms.

Based on the present invention, the above objects could be accomplished by a provision of *Lactobacillus reuteri* Probio-16 (Accession No. KCCM 10214), inhibitory of the growth of rotavirus and other pathogenic organisms.

Other objects, advantages and features of the present invention will become apparent to those skilled in the art from the following discussions.

BEST MODES FOR CARRYING OUT THE INVENTION

It has now been discovered that a novel strain, *Lactobacillus reuteri* Probio-16, which is intestinal bacterium derived from pigs and can grow under anaerobic conditions, has the effect of inhibiting the growth of rotavirus and other microorganisms, thereby preventing and treating diarrhea of mammals, for example livestock, poultry, pet animals, etc.

So, the present invention pertains to the identification and characterization of a novel enteric bacterium. Identified as a kind of *Lactobacillus reuteri* species, the novel bacterium of the present invention is characterized to be tolerant of gastric and bile acids.

This invention arose from a desire by the inventors to improve on prophylactic and therapeutic methods for treating diarrheal conditions associated with rotavirus infection in mammals, especially in humans and swines. More particularly, the present invention provides an effective and potent agent for the treatment of diarrhea and/or gastroenteritis, associated with a variety of conditions linked to rotavirus and enteric bacteria infections. The microorganism of this invention prevents and retards rotavirus infections and is effective in the treatment of diarrhea. Thus, the probiotic strain of the present invention be used for reducing the number of enteric pathogenic bacteria in food items and in the gastrointestinal tracts of animals.

In fact, it was found that the microorganism of the present invention, beside adhesion to intestinal cells often superior to the reference strains, also had the following characteristic features:

ability to inhibit the growth of rotavirus and intestinal pathogens;

ability to grow under a variety of conditions, both in aerobiosis and anaerobiosis, and at different pH values; these properties confer good capacity to adapt to the variable physiological and pathological situations that are met during the transit in the gastrointestinal tract;

production of a lactic acid;

high resistance to the gastric and bile acids;

resistance to lyophilization, without losing viability.

Moreover, the agent of this invention is devoid of the drawbacks and side effects of other known therapies.

A "probiotic" is understood to be a live or dead microbial food supplement which beneficially affects the animal, including human host by improving the individual's microbial balance in the gastrointestinal tract, e.g., *Lactobacillus reuteri* and other *Lactobacillus acidophilus*. That is, a probiotic microorganism is useful for changing the digestive system bacteria in animals when fed orally. For example, a probiotic microorganism, upon oral feeding, can rapidly reduces and replaces the natural or ingested population of bacteria in the digestive system in animals, thereby preventing recurring disorders particularly disorders in the intestine. The probiotic microorganism remains effective in the digestive system for substantial periods of time even after oral feeding is discontinued.

To search for the probiotic microorganism of the present invention, the following procedures were accomplished:

First, 1 g of swine excrements was collected into an anaerobic bag such as that manufactured by BBL, identified as "GasPak pouch", and diluted 10 fold in an anaerobic diluent of pH 2, followed by shaking for 120 min in a shaker. 1 ml of the shaken dilution was spread over a BL agar medium containing 2% of Oxgal (Difco, trade name) and incubated at 37° C. for 48 hours. After appearance of colonies on the medium, rod-shaped microorganisms were selected from 144 colonies with monitoring under a microscope and cultured in GAM-semi agar media. The cultures were stored at −80° C. until use.

Then, the selected rods(bacteria) were tested for growth inhibition of harmful microorganisms. In this regard, the following 13 pathogenic species were used for antibiotic assay according to the Kuroiwa's method (Kuroiwa et al., 1990): *Esherichia coli* KCTC 2441, *Esherichia coli* KCTC 2571, *Klebsiela pneumoniae* KCTC 2208, *Staphylococcus aureus* KCTC 1621, *Staphylococcus epidermis* KCTC 1917, *Salmonella enteritidis* kim sp14, *Shiegella flexneri* KCTC 2008, *Proteus vulgaris* KCTC 2579, *Enterobacter cloacae* KCTC 2361, *Enterococcus lactis* KCTC 1913, *Serratia marscens* KCTC 2172, *Citrobacter freundii* KCTC 2006, *Bacillus subtilis* KCTC 1021.

After the harmful microorganisms were anaerobically cultured for 18 hours in MRS broths, 1 ml of each culture was spread over MRS agar media. 30 μl of each of the selected bacteria, after being anaerobically cultured for 18 hours in the same broth, was inoculated onto a paper disc with a diameter of 8 mm. The paper discs were positioned on the MRS plates which were spread with the harmful microorganisms. Inhibitory circles emerging after a certain time period of culturing were measured. The strain which was measured to show the largest inhibitory effect compared with control groups was designated #Probio-16.

The selected strains were tested for the growth inhibition of rotavirus as follows. TF-104 monolayer cells were washed twice with phosphate buffered saline and inoculated with rotavirus. After the virus was allowed to adsorb onto the cells for 30 min, the medium was added with serum-free Eagle's Minimum Essential Medium (EMEM) and then with an appropriate amount of trypsin. While being cultured at 37° C., the infected cells were observed for cytopathic effect (CPE). When CPE was observed in about 70% of the monolayer cells, the MEM medium containing the cells was frozen at −70° C. and thawed. This freeze-thaw procedure was repeated twice. After the centrifugation of the medium, the supernatant was stored at −70° C. until use. Separately, TF-104 monolayer cells were placed on 96-well microplates and washed twice with phosphate buffered saline. After thawing the rotavirus suspension from −70° C., 10-fold serial dilutions were made. Each dilution was inoculated into 10 wells of the TF-104 monolayer cells, which were then cultured for 72 hours at 37° C. in a humidified atmosphere containing 5% $CO_2$ while observing CPE. Based on the observation results, the virus existing in the culture was quantitatively determined according to the Reed & Muench's method (Microbiology $3^{rd}$ Edition, Davis et al., Harper & Row Publishers, 1980).

In that way, the inventors have shown that #Probio-16 inhibits the in vitro infection of cells by rotaviruses as well as diarrhea and/or gastroenteritis induced by rotaviruses in an animal model. In one example of the present invention, the antiviral activity assay started with the treatment of a rotaviral culture with trypsin at 37° C. for 1 hour. The pre-treated culture was diluted with a serum-free Eagle's Minimum Essential Medium to virus titers of 1.0 $TCID_{50}$/0.1 ml, 10.0 $TCID_{50}$/0.1 ml, 100 $TCID_{50}$/0.1 ml, and 1,000 $TCID_{50}$/0.1 ml. Separately, TF-104 monolayer cells were aliquoted into wells of 96-well microplates and washed twice with phosphate buffered saline. 4 wells were allocated to one culture sample of #Probio-16. Into 4 wells, 1.0 $TCID_{50}$/0.1 ml, 10 $TCID_{50}$/0.1 ml, 100 $TCID_{50}$/0.1 ml, and 1000 $TCID_{50}$/0.1 ml were added in an amount of 90 μl, respectively, immediately followed by the addition of 10 μl (10%) of the lactobacillus culture. The cells were observed for cytopathic effect at 24, 48 and 72 hours while being cultured at 37° C. in a humidified atmosphere containing 5% $CO_2$. The identification of CPE was regarded as absence of antiviral activity.

Antibiotic susceptibility of #Probio-16 was assayed according to Microbiology procedures handbook vol. 1 (Henry D. Isenberg, ASM) and Korean Pat. Publication No. 91-4366. In this regard, 13 antibiotics, that is, cephalexcin, erythromycin, flumequinine, furazolidine, gentamycin, procaine, penicillin G, norflaxacine, spectinomycin, tetracycline, tiamuline, neomycin, chloramphenicol, and kanamycin, were dissolved in appropriate solvents. By concentrations, the prepared antibiotic solutions were inoculated in an amount of 30 μl onto a paper disc which was then allowed to stand for 1 hour at 4° C. Inhibitory circles emerging after 24 hours of anaerobic incubation were measured.

The identification of *Lactobacillus reuteri* strain is confirmed using standard microbiological and physicobiochemical tests, the taxonomic characteristics of the species and 16S rRNA sequencing.

With regard to the morphological and physicobiochemical characteristics of #Probio-16, it is a Gram-positive bacterium which can grow in both aerobic and anaerobic conditions without formation of spores, and has no motility. Its optimal temperature ranges from 30 to 37° C. This bacterium does not generate gas and indole, nor show hemolysis, nor reduce nitric acid. It cannot decompose urea and proteins, but ferments mannose and raffinose and is tolerant of 5% bile acid. This bacterium is positive for alginine dehydrolase, alginine arylamidase, proline arylamidase, leucyl glycine arylamidase, leucine arylamidase, phenylalanine arylamidase, tyrosine arylamidase, alanine arylamidase, glycine arylamidase, histidine arylamidase, serine arylamidase, alpha-galactosidase, alpha-glucosidase, beta-glucosidase, alpha-arabinosidase, and beta-glucuronidase; negative for catalase, lipase, lecithinase, alkali phosphatase, glutamate decarboxylase, pyro glutamate arylamidase, glutamyl glutamate arylamidase, 6-phosphate-beta-galactosidase, beta-N-acetyl-glucosidase, and alpha-fructosidase.

The 16S rDNA of #Probio-16 has the nucleotide sequence listed in SEQ. ID. NO. 1. Through a molecular systematic analysis based on 16S rDNA sequences, #Probio-16 was found to have 99.5% homology with the type strain of *Lactobacillus reuteri*, showing the highest phylogenetic relatedness among the strains tested. Based on these results, #Probio-16 was identified as a member of *Lactobacillus reuteri* strain and deposited at the Korean Culture Center of Microorganisms located at 361-221, Yurim B/D, Hongje-1-dong, Seodaemun-gu, Seoul, 120-091, Republic of Korea, under accession No. KCCM 10214 on Oct. 2, 2000 in accordance with the terms and provisions of the Budapest Treaty relating to deposit of microorganisms.

Also, the present invention is directed to a method for inhibiting harmful microorganisms using the novel strain. In the method, the inhibitory activity of *Lactobacillus reuteri* Probio-16 against the growth of harmful microorganisms is optimally effected at 30 to 70° C.

An experiment for antibiotic susceptibility showed that *Lactobacillus reuteri* Probio-16 is susceptible to cephalexcin with a minimal inhibitory concentration (MIC) of 90 μg/ml, erythromycin with an MIC of 4 μg/ml, flumequinine with an MIC of 4,000 μg/ml, furazolidine with an MIC of 90 μg/ml, gentamycine with an MIC of 100 μg/ml, penicillin G with an MIC of 4, norflaxacine with an aid of 100, spectinomycine with an MIC of 2,500 μg/ml, tetracycline with an MIC of 1,500 μg/ml, tiamuline with an MIC of 300 μg/ml, neomycine with an MIC of 100 µg/ml, chloramphenicol with an MIC of 200 µg/ml, and kanamycine with an MIC of 4,000 µg/ml, For stable long preservation, the microorganism of the present invention is stored at −80° C. in glycerol or freeze-dried from a suspension in 10% non-fat milk.

In addition, the present invention is directed to foods, medicines for humans and animals, and feedstock, which contain the novel microorganism. The microorganism of the present invention may be used alone, with a carrier or as an additive to a foodstuff, or in other compositions suitable for human and livestock consumption. That is, the microorganism of the present invention is useful because it can be added both to foodstuffs that do not contain probiotic bacteria (for the purpose of giving these products a probiotic value as well) and to foodstuffs already containing some probiotic bacteria (for the purpose of enhancing and/or completing their probiotic value).

A pharmaceutical, veterinary or alimentary composition of the present invention comprises the isolated *Lactobacillus reuteri* Probio-16 alone as a probiotic lactic acid bacteria or a mixture of two or more of strains mixed with an appropriate vehicle (carrier). For example, Other preferred probiotic strains that may be used in accordance with the composition of the present invention may be selected from one or more microorganisms suitable for human or animal consumption and which is able to improve the microbial balance in the human or animal intestine. Examples of suitable probiotic microorganisms include yeasts such as *Saccharomyces, Candida, Pichia* and *Torulopsis*, moulds such as *Aspergillus, Rhizopus, Mucor*, and *Penicillium* and bacteria such as the genera *Lactobacillus, Bifidobacterium, Clostridium, Leuconostoc, Bacteroides, Staphylococcus, Lactococcus, Bacillus, Streptococcus, Fusobacterium, Propionibacterium, Enterococcus, Pediococcus*, and *Micrococcus*. Specific examples of suitable probiotic micro-organisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus delbruckii, Lactobacillus johnsonii, Lactobacillus farciminus, Lactobacillus gasseri, Lactobacillus helveticus, Lactobacillus rhamnosus, Lactobacillus sake, Lactococcus lactis, Micrococcus varians, Pediococcus acidilactici*, and *Staphylococcus xylosus*. Other agents, for instance, that may be added to the composition for this particular application are bulking agents, carbon black, high fiber additives, encapsulation agents, protease inhibitors, glycosidase inhibitors, and carrier lipids, optionally miceliar, among others. These may be present in amounts known in the art. In the composition the isolated *Lactobacillus reuteri* Probio-16 is present in lyophilized form or in the form of capsules, solutions or drinkable suspensions or powder. Also, the probiotic microorganisms are preferably in powdered, dried form; especially in spore form. Further, if desired, the probiotic microorganism may be encapsulated to further increase the probability of survival.

These compositions can be administered orally or mixed with feedstock or food products such as milk, yoghurt or milk-products, juices, cereals, chewing gum, crackers, candies, vitamin supplements, meats, vegetables and fruits, blended or otherwise as baby food for example, and cookies, for the treatment or prophylaxis of gastrointestinal pathologies in which it is desirable to administer *lactobacilli*, as for example in the case of intestinal diarrhea of various origins, ulcerative colitis and related pathologies.

In another embodiment of the present invention, instead of composition the prepared cells, homogenates thereof or fractions containing the cell wall components, also may be given orally to livestock, poultry, pet animals, etc. in the form of a liquid, generally an aqueous liquid; or if necessary and desired, the microorganism may be dried to a powdery form, which is added to feed for livestock, poultry, pets, etc.

Usable instead of conventional antibiotics, the foods, medicines and feedstock of the present invention comprising the novel strain inhibit harmful intestinal microorganisms to maintain a stable balance in human and animal intestinal flora, thereby benefiting the health of humans and bringing about an improvement in weight gain, meat quality, milk production, and immunity in livestock. That is, the compositions of the present invention can also be administered in consequence of antibiotic treatments in order to preserve the non-pathological intestinal bacterial flora. Also, it will be understood that the composition of feedstuff of this invention achieves excellent results in increasing rate of weight, increased weight per a day and feed efficiency and is preferred by various domesticated animals, such as cows, swines, dogs, chickens, and etc.

Moreover, the novel anti-rotaviral microorganism of this invention is suitable for use in most instances of rotavirus infection, and particularly in cases where other therapies are either ineffective or clinically contraindicated.

So, this invention also provides a method of retarding the onset of, or countering, rotavirus infection of a subject's cells comprising administering to a subject at risk for, or suffering from, rotavirus infection an anti-rotavirus effective amount of the microorganism of this invention or mixtures thereof, or a composition comprising the microorganism of the invention and/or a pharmaceutically-acceptable carrier and/or a foodstuff and/or other additives as described above. The composition may incorporate other anti-viral or antimicrobial agents, as suitable for effective treatment of a rotavirus infection taking into account the age, general health, and nutritional status of the subject. Thus, the present invention finds its application in the prevention and treatment of diseases such as diarrhea and gastroenteritis caused by rotavitus and associated microorganisms.

The microorganism of this invention exhibits additional advantages for the treatment of livestock since, as already indicated, it is normal intestinal microflora. The present microorganism is thus unlikely to elicit toxic, immunological or allergic reactions in treated subjects.

In the present invention, livestock includes swine, cow, horse, goat, sheep, etc.; poultry includes fowls such as chicken, etc.; and pets include dogs, cats, etc.

A better understanding of the present invention may be obtained in light of the following examples which are set forth to illustrate, but are not to be construed to limit the present invention.

EXAMPLE 1

Isolation of Bacteria Tolerant of Gastric and Bile Acids

From healthy, 11 month-old female swine, excrements were anaerobically collected into a GasPak pouch (BBL). 1 g of the swine excrements was diluted 1:10 with an anaerobic diluent (a solution 0.78% $K_2HPO_4$, salt mix 37.5 ml, L-cystein 0.5 g, 25% L-ascorbic acid 2 ml, 8% $Na_2CO_3$ 50 ml, and 0.1% resazurin 1 ml in distilled sterile water 860 ml, added with agar 0.5 g) adjusted to pH 2, followed by shaking for 120 min in a shaker. 1 ml of the shaken dilution was spread over a BL agar medium containing 2% of Oxgal (Difco) and incubated at 37° C. for 48 hours. After observation of the colonies appeared on the medium with a microscope, 144 rod-shaped bacteria were selected, and cultured in GAM-semi agar media. The cultures were stored at −80° C. until use.

EXAMPLE 2

Determination of Anti-Rotaviral Activity

After being washed twice with phosphate buffered saline, TF-104 monolayer cells were inoculated with rotavirus. The rotavirus was allowed to adsorb onto the cells for 30 min, and the medium was added with serum-free Eagle's Minimum Essential Medium (EMEM) and then with an appropriate amount of trypsin. During incubation at 37° C., the infected cells were observed for cytopathic effect (CPE). When CPE was observed in about 70% of the monolayer cells, the process of freezing at −70° C. and thawing of the cell culture was repeated twice. After the centrifugation of the cell culture, the supernatant, which was free of the cells, was stored at −70° C. until use. Separately, TF-104 monolayer cells were placed on 96-well microplates and washed twice with phosphate buffered saline. The rotavirus suspension stored at −70° C. was thawed and 10-fold serial dilutions were made. Each dilution was inoculated into 10 wells of the TF-104 monolayer cells, which were then cultured for 72 hours at 37° C. in a humidified atmosphere containing 5% $CO_2$ while observing CPE. Based on the observation results, the virus existing the culture was quantitatively determined according to the Reed & Muench's method (Microbiology $3^{rd}$ Edition (Davis et al., Harper & Row Publishers, 1980)).

For the antiviral activity assay, a rotaviral culture was trypsinized at 37° C. for 1 hour and diluted with a serum-free Eagle's minimum essential medium to virus titers of 1.0 $TCID_{50}/0.1$ ml, 10.0 $TCID_{50}/0.1$ ml, 100 $TCID_{50}/0.1$ ml, and 1,000 $TCID_{50}/0.1$ ml Separately, TF-104 monolayer cells were aliquoted into wells of 96-well microplates and washed twice with phosphate buffered saline. 4 wells were allocated to one culture sample of the isolated strain. Into 4 wells, 1.0 $TCID_{50}/0.1$ ml, 10 $TCID_{50}/0.1$ ml, 100 $TCID_{50}/0.1$ ml, and 1000 $TCID_{50}/0.1$ ml were added in an amount of 90 μl, respectively, immediately followed by the addition of 10 μl (10%) of the bacterial culture. While being cultured at 37° C. in a humidified atmosphere containing 5% $CO_2$, the cells were observed for cytopathic effect at 24, 48 and 72 hours. If any CPE was observed, the culture was regarded as having no antiviral activity.

The inhibitory effects of the selected strain on rotavirus is given in Table 1, below.

TABLE 1

| | Inhibitory activity of the Selected Strain(#Probio-16) Against Rotavirus | | | |
|---|---|---|---|---|
| | 1000 $TCID_{50}$ | 100 $TCID_{50}$ | 10 $TCID_{50}$ | 1 $TCID_{50}$ |
| 24 hrs after incubation | − | − | − | − |
| 48 hrs after incubation | + | − | − | − |

TABLE 1-continued

| | Inhibitory activity of the Selected Strain(#Probio-16) Against Rotavirus | | | |
|---|---|---|---|---|
| | 1000 $TCID_{50}$ | 100 $TCID_{50}$ | 10 $TCID_{50}$ | 1 $TCID_{50}$ |
| 72 hrs after incubation | + | ± | − | − |

EXAMPLE 3

Test for Inhibitory Activity of the Isolated Strain Against Growth of Harmful Microorganisms The selected strain were tested for growth inhibition of harmful microorganisms according to the Kuroiwa's method (Kuroiwa et al., 1990), using the following 13 microorganism species that are usually used for antibiotic assay: After the harmful microorganisms were anaerobically cultured for 18 hours in MRS broths (Difco), 1 ml of each culture was spread over MRS agar media. Afterwards, 30 μl of each of the selected bacilli, after being anaerobically cultured for 18 hours in the same broth, was inoculated onto a paper disc with a diameter of 8 mm. The paper discs were positioned on the harmful microorganism-coated MRS plates. Inhibitory circles emerging after a certain time period of culturing were measured. The strain which was measured to show the largest inhibitory effect compared with control groups was called #Probio-16.

The inhibitory activity of #Probio-16 against harmful microorganisms is given in Table 2, below.

TABLE 2

Inhibitory Activity of #Probio-16 Against Microorganisms

| Harmful Microorganisms | Inhibitory Activity(diameter, mm) |
|---|---|
| Esherichia coli KCTC 2441 | 15 |
| Esherichia coli KCTC 2571 | 17 |
| Klebsiela pneumoniae KCTC 2208 | 15 |
| Staphylococcus aureus KCTC 1621 | 16 |
| Staphylococcus epidermis KCTC 1917 | 18 |
| Salmonella enteritidis kim sp14 | 16 |
| Shiegella flexneri KCTC 2008 | 16 |
| Proteus vulgaris KCTC 2579 | 15 |
| Enterobacter cloacae KCTC 2361 | 18 |
| Enterococcus lactis KCTC 1913 | 15 |
| Serratia marscens KCTC 2172 | 15 |
| Citrobacter freundii KCTC 2006 | 15 |
| Bacillus subtilis KCTC 1021 | 16 |

As apparent from the data, #Probio-16 is identified as being very effective, with similar inhibitory activity versus the 13 microorganism species. Additionally, #Probio-16 was found to be more inhibitory of harmful microorganisms than the preexisting *Lactobacillus reuteri* strain (BSA-131) disclosed in Chang et al., Kor. J. Appl. Microbiol. Biotechnol., 27, 23–27; Korean Pat. No. 10-211529-0000. Also, the novel strain of the present invention was measured to be more viable than the conventional one.

EXAMPLE 4

Susceptibility of #Probio-16 to Antibiotics

Assay of #Probio-16 for antibiotic susceptibility was conduced according to Microbiology Procedures Handbook vol. 1 (Henry D. Isenberg, ASM) and Korean Pat. Publication No. 91-4366, with regard to 13 antibiotics, including cephalexcin, erythromycin, flumequinine, furazolidine, gentamycin, procaine, penicillin G, norflaxacine, spectinomycin, tetracycline, tiamuline, neomycin, chloramphenicol, and kanamycin. By concentrations, antibiotic solutions were inoculated in an amount of 30 µl onto a paper disc which was then allowed to stand for 1 hour at 4° C. Inhibitory circles emerging after 24 hours of anaerobic incubation were measured. The results are given in Table 3, below.

TABLE 3

Antibiotic Susceptibility of #Probio-16

| Antibiotics | MIC(ug/ml) |
|---|---|
| Cephalexcin | 90 |
| Erythromycin | 4 |
| Flumequinine | 4000 |
| Furazolidine | 90 |
| Gentamycine | 100 |
| procaine Penicilline G | 4 |
| Norflaxacine | 1000 |
| Spectinomycine | 2500 |
| Tetracycline | 1500 |
| Tiamuline | 300 |
| Neomycine | 100 |
| Chloramphenicol | 200 |
| Kanamycine | 4000 |

EXAMPLE 5

Identification of #Probio-16

Strain #Probio-16 isolated in Example 1 was cultured at 37° C. in MRS media (Difco). To identify #Probio-16, its morphology and physicobiochemistry were characterized according to the Yoon's method (Yoon et al., Int. J. Syst. Bacteriol., 47, 904, 1997) with the aid of API 32A and CHL kits (Biomerio) and its 16S rDNA were sequenced and analyzed according to the Yoon's method (Yoon et al., Int. J. Syst. Bacteriol., 47, 933, 1997).

Morphological and physicobiochemical characteristics of #Priobio-16 are summarized in Table 4, below.

TABLE 4

Morphological and Physicochemical Characteristics of #Probio-16

| Characteristics | Results |
|---|---|
| Aerotolerance | + |
| Catalase | − |
| Hemolysis | − |
| OF test | F |
| Motility | − |
| Gas formation | − |
| Spore formation | − |
| Lipase | − |
| Lecithinase | − |
| Protein degradation | − |
| Alkaline phosphatase | − |
| Urease | − |
| Indole formation | − |
| Nitrate reduction | − |
| Alginine dehydrolase | + |
| Alginine aryamidase | + |
| Proline aryamidase | + |
| Leucyl glycine aryamidase | + |
| Leucine arylamidase | + |
| Phenylalanine arylamidase | + |
| Tyrosine arylamidase | + |
| Alanine arylamidase | + |
| Glycine arylamidase | + |
| Histidine arylamidase | + |
| Serine arylamidase | + |
| Glutamate decarboxylase | − |
| Pyro glutamate arylamidase | − |
| Glutamyl glutamate arylamidase | − |
| Alpha-galactosidase | + |
| Beta-galactosidase | + |
| 6-Phosphate-beta-galactosidase | − |
| Alpha-glucosidase | + |
| Beta-glucosidase | + |
| Alpha-arabinosidase | + |
| Beta-glucuronidase | + |
| Beta-N-acetyl-glucosaminidase | − |
| Alpha-Fructosidase | − |
| Mannose fermentation | + |
| Raffinose fermentation | + |
| Resistance to bile acids(5%) | + |

+ positive;
− negative

As seen in Table 4, #Probio-16 is a Gram-positive bacterium which can grow in both aerobic and anaerobic conditions without formation of spores, and has no motility. Its optimal growth temperature ranges from 30 to 37° C. This strain does not generate gas and indole, nor show hemolysis, nor reduce nitric acid. It cannot decompose urea and proteins, but ferments mannose and raffinose and is tolerant of 5% bile acid and positive for alginine dehydrolase, alginine arylamidase, and proline arylamidase.

The 16S rDNA of #Probio-16 has the nucleotide sequence listed in SEQ. ID. NO. 1.

Through a molecular systematic analysis based on 16S rDNA sequences, #Probio-16 was found to have 99.5% homology with the type strain of *Lactobacillus reuteri*, showing the highest phylogenetic relatedness among the strains tested. Also, it was found that #Probio-16 is different from the preexisting probiotic BSA-131 in two nucleotide sequences. Based on these results, #Probio-16 was identified as a novel *Lactobacillus reuteri* strain and deposited in the Korean Culture Center of Microorganisms under accession No. KCCM 10214 on Oct. 2, 2000.

INDUSTRIAL APPLICABILITY

As described hereinbefore, the novel strain of the present invention has inhibitory activity against rotavirus and pathogenic bacteria, as well as being tolerant of gastric and bile acid. Useful as a probiotic which can substitute for conventional antibiotics, therefore, the novel strain of the present invention inhibits harmful intestinal microorganisms to maintain a stable balance in human and animal intestinal flora, thereby benefiting the health of humans and bringing about an improvement in weight gain, meat quality, milk production, and immunity in livestock.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

The invention claimed is:

1. *Lactobacillus reuteri* Probio-16 (Accession No. KCCM 10214), inhibitory of the growth of rotavirus and other pathogenic organisms.

2. A pharmaceutical, veterinary, or alimentary composition comprising an effective amount of probiotic *Lactobacillus reuteri* Probio-16 as defined in claim 1 and a carrier.

3. The composition of claim 2 wherein the composition is useful for changing the digestive system bacteria in mammals including humans, when fed orally.

4. The composition of claim 2 wherein the composition is useful for the treatment of diarrhea in mammals including humans, when fed orally.

5. A feedstock or food composition including an effective amount of the probiotic composition as defined in claim 2.

6. A method for reducing the incidence of or treating infectious diarrhea in mammals, including human, said method comprising enterally administering an effective amount of *Lactobacillus reuteri* Probio-16 as defined in claim 1.

7. A method for reducing the incidence of or treating infectious diarrhea in mammals, including human, said method comprising enterally administering the probiotic composition defined in claim 2 to said mammals.

8. A method for retarding the onset of or treating an infection caused by rotaviruses in mammals, including human, said method comprising enterally administering an effective amount of *Lactobacillus reuteri* Probio-16 as defined in claim 1.

9. A method for retarding the onset of or treating an infection caused by rotaviruses in mammals, including human, said method comprising enterally administering the probiotic composition defined in claim 2 to said mammals.

* * * * *

SEQUENCE LISTING

<160> NUMBER OF SEQ ID NOS: 1

<210> SEQ ID NO 1
<211> LENGTH: 1531
<212> TYPE: DNA
<213> ORGANISM: Lactobacillus reuteri

<400> SEQUENCE: 1

```
gatgaacgcc ggcggtgtgc ctaatacatg caagtcgtac gcactggccc aactgattaa       60
tggtgcttgc acctgattga cgatggatca ccagtgagtg gcggacgggt gagtaacacg      120
taggtaacct gccccggagc gggggataac atttggaaac agatgctaat accgcataac      180
aacaaaagcc acatggcttt tgtttgaaag atggctttgg ctatcactct gggatggacc      240
tgcggtgcat tagctagttg gtaaggtaac ggcttaccaa ggcgatgatg catagccgag      300
ttgagagact gatcggccac aatggaactg agacacggtc catactccta cgggaggcag      360
cagtagggaa tcttccacaa tgggcgcaag cctgatggag caacaccgcg tgagtgaaga      420
agggtttcgg ctcgtaaagc tctgttgttg gagaagaacg tgcgtgagag taactgttca      480
cgcagtgacg gtatccaacc agaaagtcac ggctaactac gtgccagcag ccgcggtaat      540
acgtaggtgg caagcgttat ccggatttat tgggcgtaaa gcgagcgcag gcggttgctt      600
aggtctgatg tgaaagcctt cggcttaacc gaagaagtgc atcggaaacc gggcaacttg      660
agtgcagaag aggacagtgg aactccatgt gtagcggtgg aatgcgtaga tatatggaag      720
aacaccagtg gcgaaggcgg ctgtctggtc tgcaactgac gctgaggctc gaaagcatgg      780
gtagcgaaca ggattagata ccctggtagt ccatgccgta acgatgagt gctaggtgtt      840 ggagggtttc cgcccttcag tgccggagct aacgcattaa gcactccgcc tggggagtac      900
gaccgcaagg ttgaaactca aaggaattga cgggggcccg cacaagcggt ggagcatgtg      960
gtttaattcg aagctacgcg aagaacctta ccaggtcttg acatcttgcg ctaaccttag     1020
agataaggcg ttcccttcgg ggacgcaatg acaggtggtg catggtcgtc gtcagctcgt     1080
gtcgtgagat gttgggttaa gtcccgcaac gagcgcaacc cttgttacta gttgccagca     1140
ttaagttggg cactctagtg agactgccgg tgacaaaccg gaggaaggtg gggacgacgt     1200
cagatcatca tgccccttat gacctgggct acacacgtgc tacaatggac ggtacaacga     1260
gtcgcaagct cgcgagagta agctaatctc ttaaagccgt tctcagttcg gactgtaggc     1320
tgcaactcgc ctacacgaag tcggaatcgc tagtaatcgc ggatcagcat gccgcggtga     1380
atacgttccc gggccttgta cacaccgccc gtcacaccat gggagtttgt aacgcccaaa     1440
gtcggtggcc taaccattat ggagggagcc gcctaaggcg gacagatga ctggggtgaa     1500 gtcgtaacaa ggtagccgta ggagaacctg c                                    1531
```